United States Patent
Abe et al.

(10) Patent No.: US 12,357,612 B2
(45) Date of Patent: Jul. 15, 2025

(54) PROPHYLACTIC OR THERAPEUTIC AGENT FOR CANCER

(71) Applicants: TOHOKU UNIVERSITY, Miyagi (JP); KAKE EDUCATIONAL INSTITUTION, Okayama (JP)

(72) Inventors: Takaaki Abe, Miyagi (JP); Shinobu Ohnuma, Miyagi (JP); Michiaki Unno, Miyagi (JP); Kenichiro Hayashi, Okayama (JP)

(73) Assignees: TOHOKU UNIVERSITY, Miyagi (JP); KAKE EDUCATIONAL INSTITUTION, Okayama (JP)

( * ) Notice: Subject to any disclaimer, the term of this patent is extended or adjusted under 35 U.S.C. 154(b) by 915 days.

(21) Appl. No.: 17/442,173

(22) PCT Filed: Mar. 25, 2020

(86) PCT No.: PCT/JP2020/013411
§ 371 (c)(1),
(2) Date: Sep. 23, 2021

(87) PCT Pub. No.: WO2020/196651
PCT Pub. Date: Oct. 1, 2020

(65) Prior Publication Data
US 2022/0175724 A1 Jun. 9, 2022

(30) Foreign Application Priority Data
Mar. 28, 2019 (JP) .................. 2019-063638

(51) Int. Cl.
*A61K 31/405* (2006.01)
*A61K 9/00* (2006.01)
*A61P 35/00* (2006.01)

(52) U.S. Cl.
CPC .......... *A61K 31/405* (2013.01); *A61K 9/0053* (2013.01); *A61P 35/00* (2018.01)

(58) Field of Classification Search
CPC ..... A61K 31/405; A61K 9/0053; A61P 35/00; A61P 1/04; A61P 35/02; A61P 43/00
See application file for complete search history.

(56) References Cited

FOREIGN PATENT DOCUMENTS

| | | | |
|---|---|---|---|
| JP | 2012513462 A | | 6/2012 |
| JP | 2015519388 A | | 7/2015 |
| JP | 2015189670 A | * | 11/2015 |
| JP | 2016-6115 A | | 1/2016 |
| JP | 2018030807 A | | 3/2018 |

OTHER PUBLICATIONS

Kanehara, Keigo et al. "The indole compound MA-35 attenuates tomorigenesis in an inflammation-induced colon cancer model" Scientific Report, Sep. 4, 2019, 9:12739.

International Search Report, PCT/JP2020/013411 [ISA/JP] dated May 26, 2020.
Caric, Dejana "Absorption and fluorescence spectra of ring-substituted indole-3-acetic acids", Biophysical Chemistry, 2004, vol. 111, pp. 247-257.
Rossiter, Sharon "Halogenated Indole-3-acetic Acids as Oxidatively Activated Prodrugs with Potential for Targeted Cancer Therapy", Bioorganic & Medicinal Chemistry Letters, 2002, vol. 12, pp. 2523-2526.
Greco, Olga "Horseradish Peroxidase-mediated Gene Therapy: Choice of Prodrugs in Oxic and Anoxic Tumor Conditions", Molecular Cancer Therapeutics, 2001, vol. 1, pp. 151-160.
Folkes, Lisa K. "Oxidative activation of indole-3-acetic acids to cytotoxic species a potential new role for plant auxins in cancer therapy", Biochemical Pharmacology, 2001, vol. 61, pp. 129-136.
Folkes, Lisa K. "Enhancing the Efficacy of Photodynamic Cancer Therapy by Radicals from Plant Auxin (Indole-3-Acetic Acid)", Cancer Research, 2003, vol. 63, pp. 776-779.
Boyle et al. "Mitochondria-targeted drugs stimulate mitophagy and abrogate colon cancer cell proliferation" J. Biol. Chem., pp. 1-28, Aug. 7, 2018.

(Continued)

*Primary Examiner* — Joseph K McKane
*Assistant Examiner* — Meghan C Heasley
(74) *Attorney, Agent, or Firm* — Edwin S. Flores; Daniel J. Chalker; Chalker Flores, LLP

(57) ABSTRACT

An object of the present invention is to provide a low molecular weight compound having a prophylactic or therapeutic action on cancer. A compound of the following formula (1), a compound of the following formula (2), or the like can be administered by a method such as oral administration to prevent or treat cancers such as colorectal cancer.

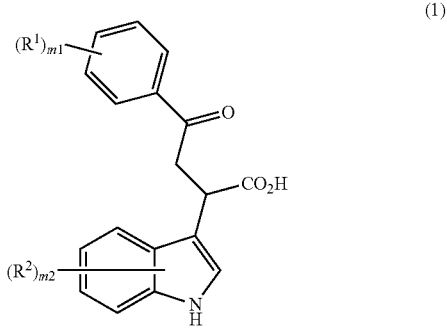

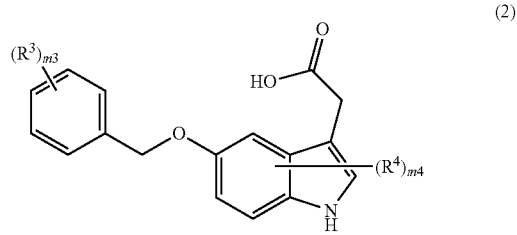

4 Claims, 2 Drawing Sheets

(56) References Cited

OTHER PUBLICATIONS

Liu et al. "Expression and clinical significance of receptor of advanced glycation end-products and transforming growth factor-β1 in tumor tissues of elderly patients with type 2 diabetes complicated with colon cancer" Chinese Journal of Gerontology, vol. 39, p. 1334~1337, Mar. 25, 2019.

Lei et al. "Mitochonic acid 5 activates the MAPK-ERK-yap signaling pathways to protect mouse microglial BV-2 cells against TNFα-induced apoptosis via increased Bnip3-related mitophagy" Cellular & Molecular Biology Letters, 23:1 pp. 1-16 Apr. 5, 2018.

Popivanova et al. "Blocking TNF-α in mice reduces colorectal carcinogenesis associated with chronic colitis" J. Clin. Invest., vol. 118, No. 2, pp. 560-570, Feb. 2008.

Shima et al. "A novel indole compound MA-35 attenuates renal fibrosis by inhibiting both TNF-α and TGF-β1 pathways" Scientific Reports, 7: 1884 pp. 1-11 May 15, 2017.

Haabeth, Ole Audun Werner, et al. "Inflammation driven by tumour-specific Th1 cells protects against B-cell cancer." Nature communications 2.1 (2011): 240. https://doi.org/10.1038/ncomms1239.

Haneda, Sho "Effect of anti TNF-a antibody against colon cancer: Does anti TNF-a antibody inhibits growth of colon Cancer?," Grants-in-Aid for Scientific Research (KAKENHI), Report on Research Progress, May 28, 2015.

Josephs, Steven F., et al. "Unleashing endogenous TNF-alpha as a cancer immunotherapeutic." Journal of translational medicine 16 (2018): 1-8. https://doi.org/10.1186/s12967-018-1611-7.

\* cited by examiner

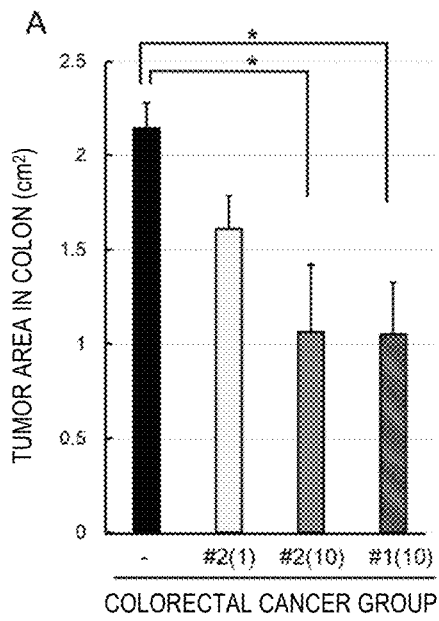
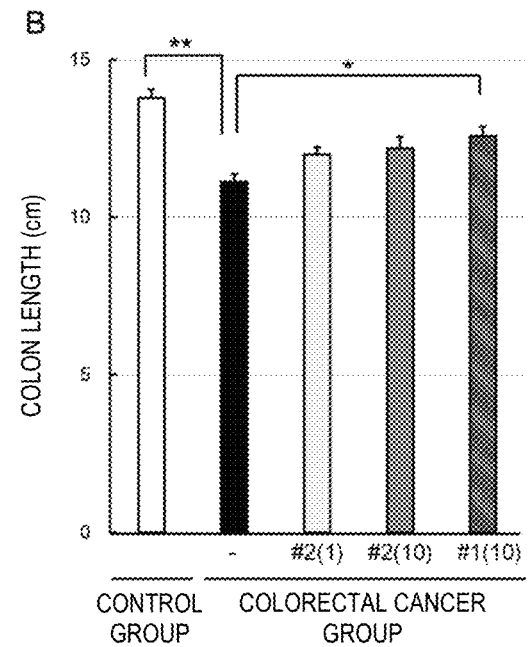
FIG. 1A
FIG. 1B
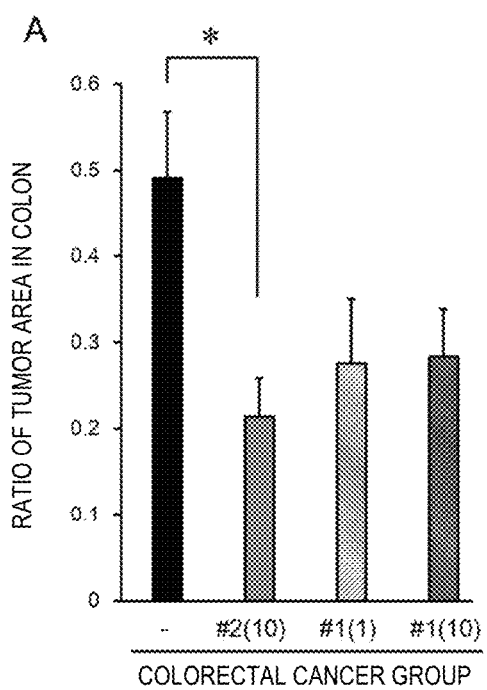
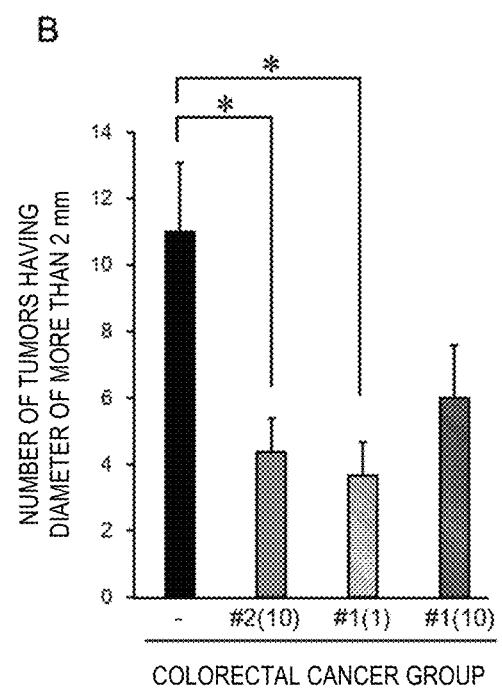
FIG. 2A
FIG. 2B

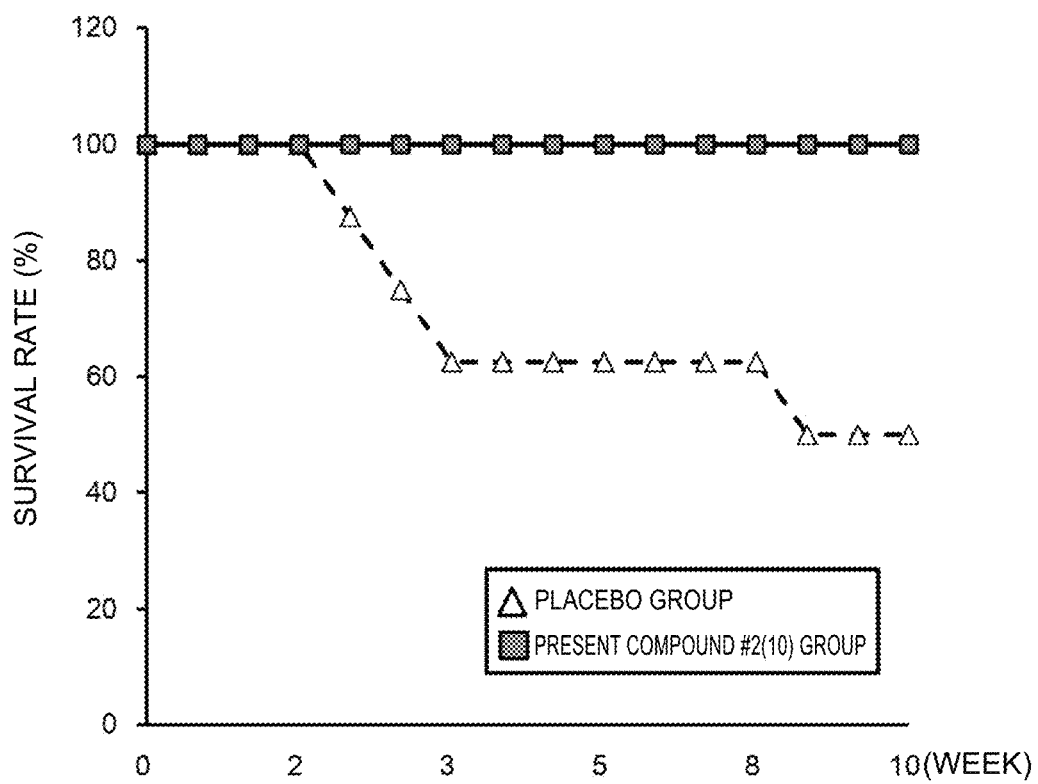
FIG. 3
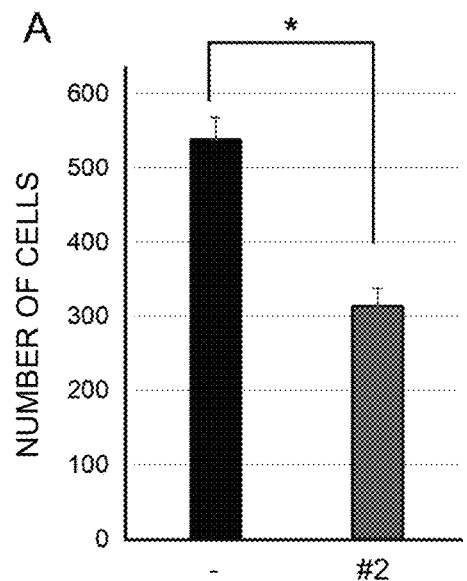 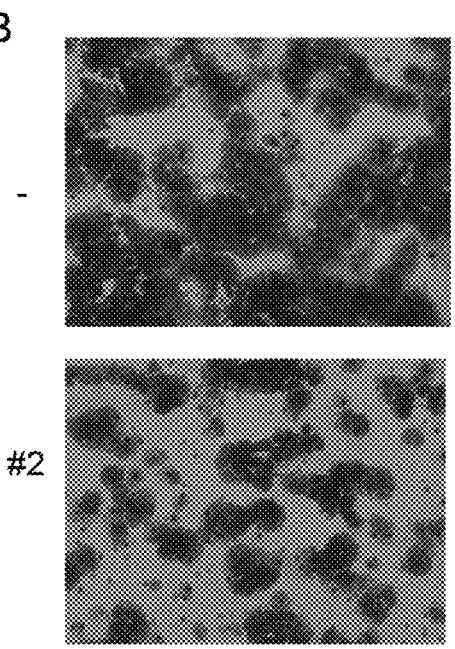
FIG. 4A　　　FIG. 4B

PROPHYLACTIC OR THERAPEUTIC AGENT FOR CANCER

CROSS-REFERENCE TO RELATED APPLICATIONS

This application is the National Stage of International Application No. PCT/JP2020/013411, filed on Mar. 25, 2020 claiming the priority of JP 2019-063638, filed on Mar. 28, 2019, the content of each of which is incorporated by reference herein.

TECHNICAL FIELD

The present invention relates to a preparation for preventing or treating cancer.

BACKGROUND OF THE INVENTION

In the age-adjusted mortality rate of Japanese for major causes of death in the Ministry of Health, Labour and Welfare's "Vital Statistics", malignant neoplasms (cancer) have been ranked first from 1981 to the present, and the mortality rate due to cancer has not shown any downward trend until recent years, and has been flat to up slightly.

The most common feature among cancer cells is that they exhibit rapid and uncontrolled growth compared to normal cells. Taking advantage of this feature, chemotherapy for cancer using a drug that is toxic to proliferative cells (that is, an anti-cancer drug) is performed. As such agents, inhibitors of nucleic acid synthesis (for example, cyclophosphamide), antibiotics (for example, actinomycin D and bleomycin), antimetabolites (for example, 5-fluorouracil and methotrexate), microtubule depolymerization inhibitors (for example, Paclitaxel), molecular targeted drugs (for example, imatinib and gefitinib) and the like are known. However, these drugs have the problem that a sufficient therapeutic effect on cancer is not always obtained.

On the other hand, the present inventors have reported that the present group of compounds described later is useful for an enhancing effect on the expression of erythropoietin and in the treatment of mitochondrial disease (patent document 1), and that it has a suppressive effect on collagen production and is useful in the treatment of fibrotic skin disease (patent document 2). However, it was previously unknown that the present group of compounds has a prophylactic or therapeutic effect on cancer.

SUMMARY OF THE INVENTION

Object to be Solved by the Invention

An object of the present invention is to provide a low molecular weight compound having a prophylactic or therapeutic action on cancer.

Means to Solve the Object

The present inventors are continuing extensive research to solve the above object. In the process, the compound (4-(2, 4-difluorophenyl)-2-(1H-indole-3-yl)-4-oxo-butanoic acid; referred to as Compound #5 in patent document 1) and the compound (5-(3,5-dimethoxybenzyloxy)-3-indoleacetic acid; referred to as compound #35 in patent document 1) of patent document 1 have been focused on and studied. As a result, they have found that specific indole derivatives, that is, the compounds of the following formulas (1) and (2), and pharmacologically acceptable salts thereof (hereinafter, may be referred to as "the present group of compounds") are useful in the prevention or treatment of cancer, and the present invention was completed.

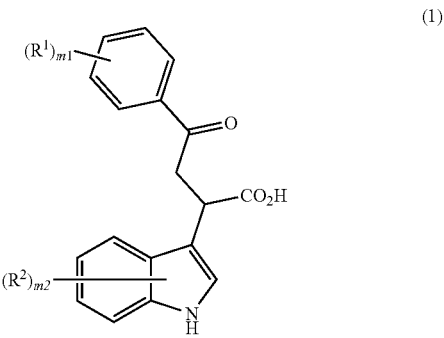

(wherein $R^1$ and $R^2$ are the same or different, and each represent a halogen atom, a C1-C6 alkyl group, a C2-C6 alkenyl group, a C2-C6 alkynyl group, or an organic oxy group represented by $OR^X$; and m1 is an integer of 0 to 5, and m2 is an integer of 0 to 5.)

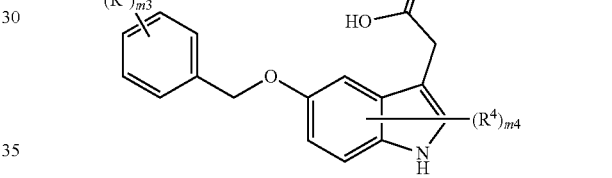

(wherein $R^3$ and $R^4$ are the same or different, and each represent a halogen atom, a C1-C6 alkyl group, a C2-C6 alkenyl group, a C2-C6 alkynyl group, or an organic oxy group represented by $OR^X$; and m3 is an integer of 0 to 5, and m4 is an integer of 0 to 4.)

That is, the present invention is as follows.

[1] A prophylactic or therapeutic agent for cancer, comprising one or more compounds selected from the compounds of the following formula (1):

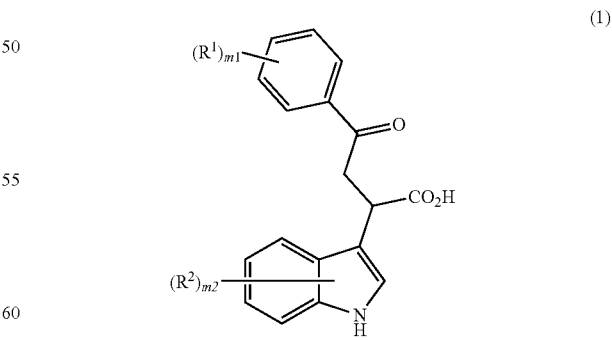

(wherein $R^1$ and $R^2$ are the same or different, and each represent a halogen atom, a C1-C6 alkyl group, a C2-C6 alkenyl group, a C2-C6 alkynyl group, or an organic oxy group represented by $OR^X$; and m1 is an integer of 0 to 5, and m2 is an integer of 0 to 5.) and the following formula (2):

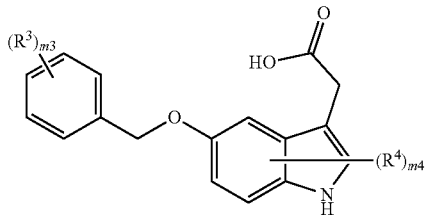

(wherein $R^3$ and $R^4$ are the same or different, and each represent a halogen atom, a C1-C6 alkyl group, a C2-C6 alkenyl group, a C2-C6 alkynyl group, or an organic oxy group represented by $OR^X$; and m3 is an integer of 0 to 5, and m4 is an integer of 0 to 4.)

and pharmacologically acceptable salts thereof.

[2] The prophylactic or therapeutic agent according to the above [1], wherein the compound of the formula (1) is a compound of the following formula (1'), and the compound of the formula (2) is a compound of the following formula (2'):

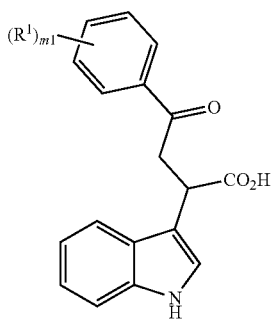

(wherein $R^1$ is the same or different, and each represents a halogen atom; and m1 is an integer of 1 to 3.)

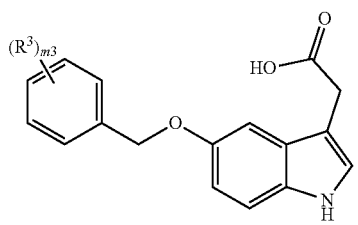

(wherein $R^3$ is the same or different, and each represents an organic oxy group represented by $OR^X$; and m3 is an integer of 1 to 3.)

[3] The prophylactic or therapeutic agent according to the above [2], wherein the compound of the formula (1') is a compound of the following formula (1-1), and the compound of the formula (2') is a compound of the following formula (2-1):

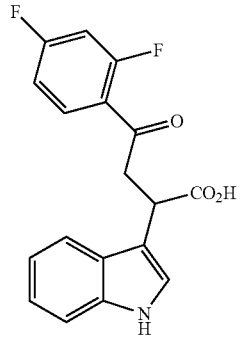

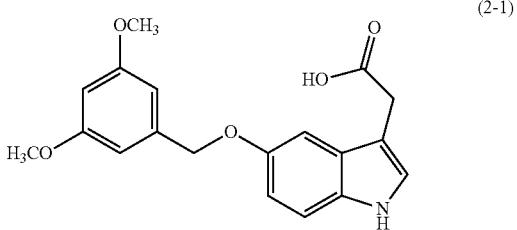

[4] The prophylactic or therapeutic agent according to any one of the above [1] to [3], wherein the cancer is a colorectal cancer.

[5] The prophylactic or therapeutic agent according to any one of the above [1] to [4], which is orally administered.

In addition, examples of other embodiments of the present invention include a method for preventing or treating cancer comprising a step of administering one or more compounds selected from the present group of compounds to a subject in need of prevention or treatment of cancer; one or more compounds selected from the present group of compounds for use as a prophylactic or therapeutic agent for cancer; one or more compounds selected from the present group of compounds for use in the prevention or treatment of cancer; and use of one or more compounds selected from the present group of compounds for producing a prophylactic or therapeutic agent for cancer.

Effect of the Invention

The present group of compounds has a prophylactic or therapeutic effect on cancer, for example, a suppressive effect on the growth of cancer cells associated with the onset of cancer, an improving effect on the decrease in survival rate due to cancer, and a suppressive effect on cancer metastasis. In addition, since the present group of compounds is composed of low molecular weight compounds that can be produced relatively easily, it is also excellent in that it can be produced relatively easily and inexpensively. Furthermore, the present group of compounds, which is composed of low molecular weight compounds, is expected to cross the blood-brain barrier (BBB), and is expected to also have a prophylactic or therapeutic effect on cancer of the nervous system.

BRIEF DESCRIPTION OF DRAWINGS

FIG. 1A is a diagram showing the results (mean±standard deviation) of analyzing the tumor area in the colons of four colorectal cancer groups (placebo group ["–" in the diagram; n=7], Present Compound #2[1] group ["#2(1)" in the diagram; n=7], Present Compound #2[10] group ["#2(10)" in the diagram; n=7], and Present Compound #1[10] group ["#1(10)" in the diagram; n=7]). FIG. 1B is a diagram showing the results (mean±standard deviation) of analyzing the colon lengths of the control group (n=8) and the above four colorectal cancer groups. "*" and "**" in the diagram indicate that there is a statistically significant difference (p<0.05 and p<0.01), respectively.

FIG. 2A is a diagram showing the results (mean±standard deviation) of analyzing the ratio of tumor area in the colons of four colorectal cancer groups (placebo group; n=4, Present Compound #2[10] group ["#2(10)" in the diagram; n=8], Present Compound #1[1] group ["#1(1)" in the diagram; n=6], and Present Compound #1[10] group ["#1(10)" in the diagram; n=5]). FIG. 2B is a diagram showing the results (mean±standard deviation) of analyzing the number of tumors having a diameter of more than 2 mm for the above four colorectal cancer groups. "*" in the diagram indicates that there is a statistically significant difference (p<0.05).

FIG. 3 is a diagram showing the results of analyzing the survival rate of two colorectal cancer groups (placebo group ["–" in the diagram; n=4] and Present Compound #2[10] group; n=8).

FIG. 4A is a diagram showing the results (mean±standard deviation) of measuring the cell migration level when culturing cells of the colorectal cancer cell line HCT116 in the presence of the Present Compound #2 ("#2" in the diagram; n=3) or absence of the Present Compound #2 ("–" in the diagram; n=3). The "number of cells" on the vertical axis indicates the number of cells whose migration ability was confirmed by a cell migration test. "*" in the diagram indicates that there is a statistically significant difference (p<0.05). FIG. 4B is a microscopic image used for the measurement of FIG. 4A.

DETAILED DESCRIPTION OF THE INVENTION

The prophylactic or therapeutic agent for cancer of the present invention is a preparation containing one or more compounds selected from the present group of compounds, which is specified for the purpose of "preventing or treating cancer" (hereinafter, may be referred to as "the present prophylactic/therapeutic agent"). Here, "preventing cancer" means preventing the onset of cancer; preventing the growth or metastasis of cancer; preventing the progression of a cancer stage; and the like. Moreover, "treating cancer" means that the growth of cancer cells in a living body is suppressed; the proportion of cancer cells in a living body is reduced; the aggravation of cancer symptoms is suppressed; the cancer symptoms are improved; and the like by a suppressive or reducing action on the growth or metastasis of cancer cells, killing cancer cells, and the like. The present prophylactic/therapeutic agent may be used alone as a medicament (preparation), or may be further mixed with an additive and used in the form of a composition (pharmaceutical composition).

In the present invention, the compounds selected from the present group of compounds mean compounds of the following formulas (1) and (2), and pharmacologically acceptable salts thereof:

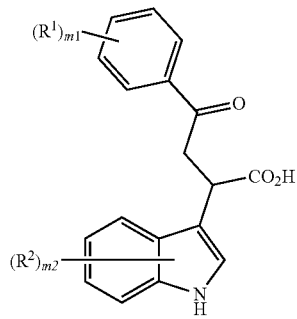

wherein $R^1$ and $R^2$ are the same or different, and each represent a halogen atom, a C1-C6 alkyl group, a C2-C6 alkenyl group, a C2-C6 alkynyl group, or an organic oxy group represented by $OR^X$; and m1 is an integer of 0 to 5, and m2 is an integer of 0 to 5.

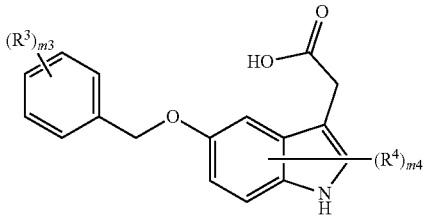

wherein $R^3$ and $R^4$ are the same or different, and each represent a halogen atom, a C1-C6 alkyl group, a C2-C6 alkenyl group, a C2-C6 alkynyl group, or an organic oxy group represented by $OR^X$; and m3 is an integer of 0 to 5, and m4 is an integer of 0 to 4.

Examples of the halogen atom in the formulas (1) and (2) include a fluorine atom, a chlorine atom, a bromine atom and an iodine atom.

The C1-C6 alkyl group in the formulas (1) and (2) means a linear or branched alkyl group having 1 to 6 carbon atoms and optionally having a substituent. Specific examples thereof include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a neopentyl group, 1,1-dimethylpropyl, 1-ethylpropyl, an n-hexyl group, a 2-methylpentyl group, a 3-methylpentyl group, a 2,2-dimethylbutyl group, and a 2,3-dimethylbutyl group.

The C2-C6 alkenyl group in the formulas (1) and (2) means a linear or branched alkenyl group having 2 to 6 carbon atoms and optionally having a substituent. Specific examples thereof include an ethenyl group (vinyl group), a 1-propenyl group, a 2-propenyl group (allyl group), a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, and a 3-hexenyl group.

The C2-C6 alkynyl group in the formulas (1) and (2) means a linear or branched alkynyl group having 2 to 6 carbon atoms and optionally having a substituent. Specific examples thereof include an ethynyl group, a 1-propynyl group, a 1-butynyl group, a 1-pentynyl group, and a 1-hexynyl group.

The $R^X$ in the organic oxy group represented by $OR^X$ of the formulas (1) and (2) is a C1-C6 alkyl group, a C2-C6 alkenyl group, or a C2-C6 alkynyl group. Moreover, the C1-C6 alkyl group, the C2-C6 alkenyl group, and the C2-C6 alkynyl group in $R^X$ have the same definitions as the C1-C6 alkyl group, the C2-C6 alkenyl group, and the C2-C6 alkynyl group described above.

Examples of the substituent in the above "optionally having a substituent" include a halogen atom, a hydroxyl group, a carboxyl group, an alkyl group having 1 to 6 carbon atoms, an alkenyl group having 2 to 6 carbon atoms, an alkynyl group having 2 to 6 carbon atoms, and a C6-C10 aryl group. The above halogen atom, alkyl group having 1 to 6 carbon atoms, alkenyl group having 2 to 6 carbon atoms, and alkynyl group having 2 to 6 carbon atoms are the same as the halogen atom, the alkyl group having 1 to 6 carbon atoms, the alkenyl group having 2 to 6 carbon atoms, and the alkynyl group having 2 to 6 carbon atoms in the formulas (1) and (2). In addition, examples of the above C6-C10 aryl group include a phenyl group and a naphthyl group.

The compound of formula (1) in the present group of compounds contains asymmetric carbons and therefore has optical isomers and racemic forms. All the optically active and racemic forms are also included within the scope of the present invention. In addition, if the compound of the present invention of formula (1) has isomers other than optical isomers (for example, position isomers and tautomers), solvates such as hydrates, crystalline polyforms, and esters (for example, an ester of the compound of the present invention of formula (1) and methanol, ethanol, n-propanol, isopropanol, n-butanol, isobutanol, sec-butanol, or tert-butanol), all of these compounds are included within the scope of the present invention.

Moreover, a compound in which one or more atoms constituting the compound of the present invention of formula (1) are isotopes, a pharmaceutically acceptable salt of the compound, a pharmaceutically acceptable ester of the compound, and a hydrate of the compound, as well as the optical isomers thereof are also included in the present invention. Examples of the isotopes contained in the compound of the present invention include isotopes of hydrogen, carbon, nitrogen, oxygen, fluorine, bromine, and chlorine, such as $^2H$, $^3H$, $^{11}C$, $^{13}C$, $^{14}C$, $^{13}N$, $^{15}N$, $^{15}O$, $^{17}O$, $^{18}O$, $^{18}F$, $^{75}Br$, $^{76}Br$, $^{77}Br$, $^{82}Br$, and $^{37}Cl$.

Of the compounds of formula (1) in the present group of compounds, the compound of the following formula (1') or a salt thereof is preferable.

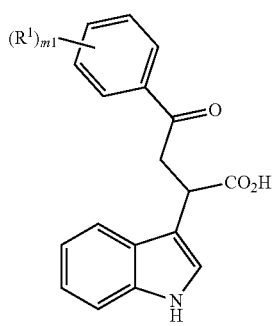

(1')

In the above formula (1'), $R^1$ and m1 have the same definitions as $R^1$ and m1 in the formula (1). In addition, $R^1$ is preferably a halogen atom, and m1 is preferably 1 to 3, more preferably 2. Furthermore, the substitution position of $R^1$ may be any of the ortho position, the meta position, and the para position with respect to the adjacent carbonyl group, but the ortho position and the para position are preferable.

If the compound of formula (2) in the present group of compounds has various isomers (for example, position isomers and tautomers), solvates such as hydrates, crystalline polyforms, and esters (for example, an ester of the compound of the present invention of formula (1) and methanol, ethanol, n-propanol, isopropanol, n-butanol, isobutanol, sec-butanol, or tert-butanol), all of these compounds are included within the scope of the present invention.

Moreover, a compound in which one or more atoms constituting the compound of the present invention of formula (2) are isotopes, a pharmaceutically acceptable salt of the compound, a pharmaceutically acceptable ester of the compound, and a hydrate of the compound, as well as the optical isomers thereof are also included in the present invention. Examples of the isotopes contained in the compound of the present invention include isotopes of hydrogen, carbon, nitrogen, oxygen, fluorine, bromine, and chlorine, such as $^2H$, $^3H$, $^{11}C$, $^{13}C$, $^{14}C$, $^{13}N$, $^{15}N$, $^{15}O$, $^{17}O$, $^{18}O$, $^{18}F$, $^{75}Br$, $^{76}Br$, $^{77}Br$, $^{82}Br$, and $^{37}Cl$.

Of the compounds of formula (2) in the present group of compounds, the compound of the following formula (2') or a salt thereof is preferable.

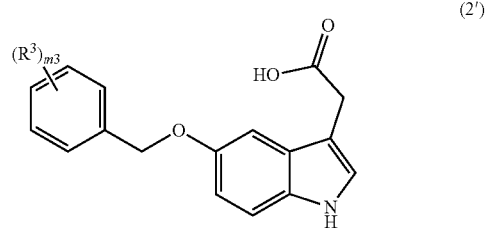

(2')

In the above formula (2'), $R^3$ and m3 have the same definitions as $R^3$ and m3 in the formula (2). In addition, $R^3$ is preferably an organic oxy group represented by $OR^X$, and more preferably a methoxy group, an ethoxy group, an n-propoxy group and an isopropoxy group. The above m3 is preferably 1 to 3, and more preferably 2. Furthermore, the substitution position of $R^3$ may be any of the ortho position, the meta position, and the para position with respect to the adjacent carbonyl group, but the meta position is preferable.

Specific examples of the compound of formula (1) include the compounds shown below.

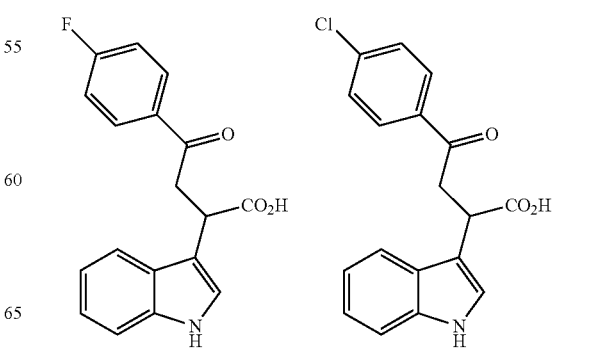

(1-1)

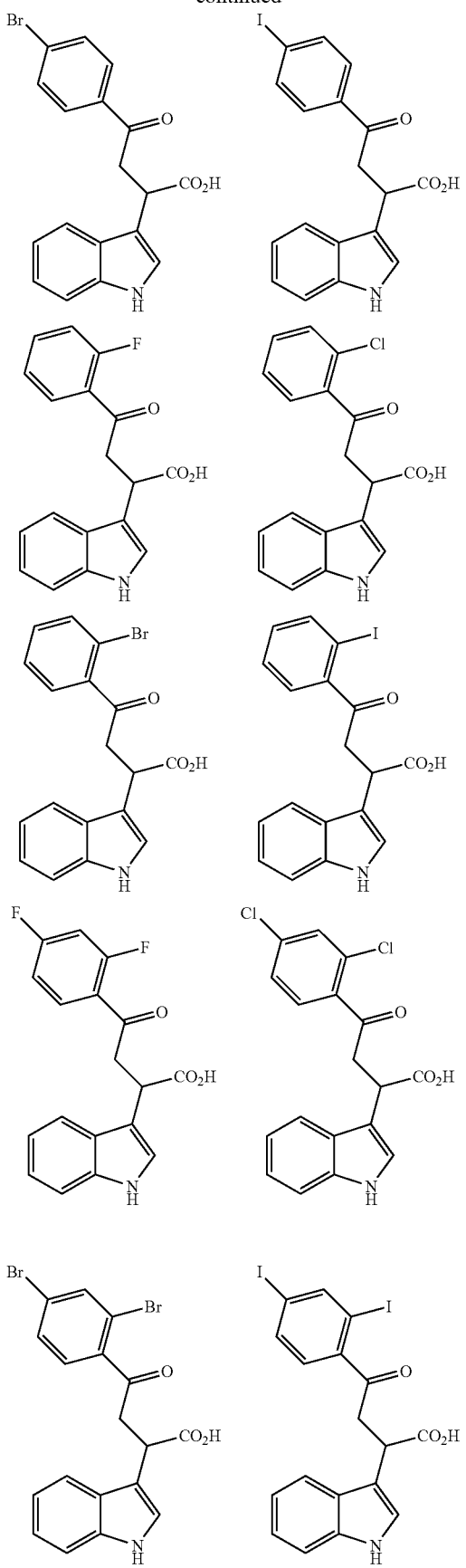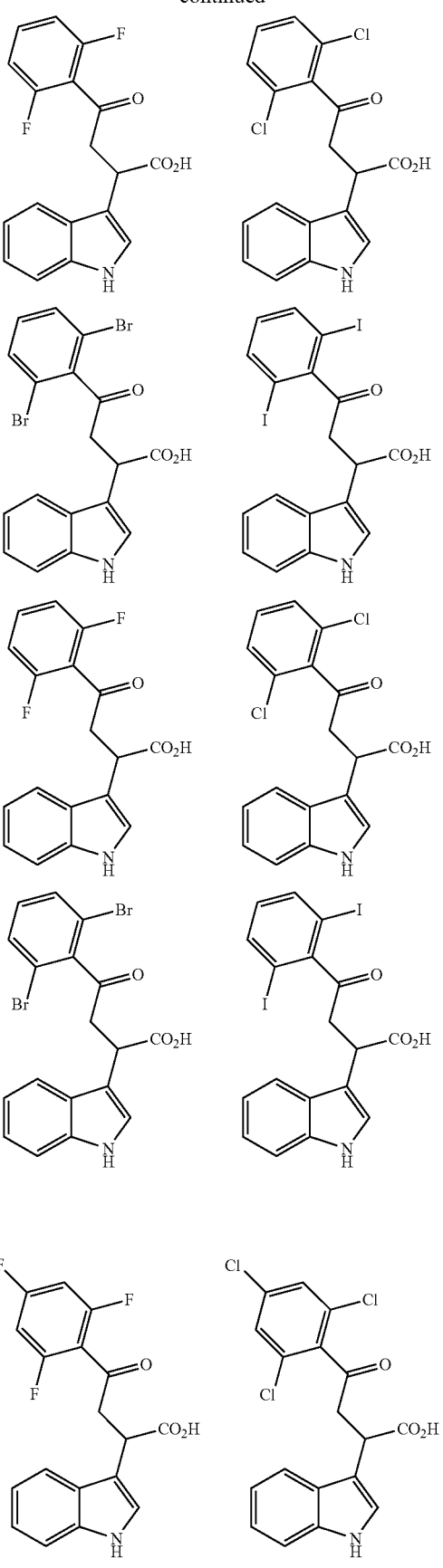

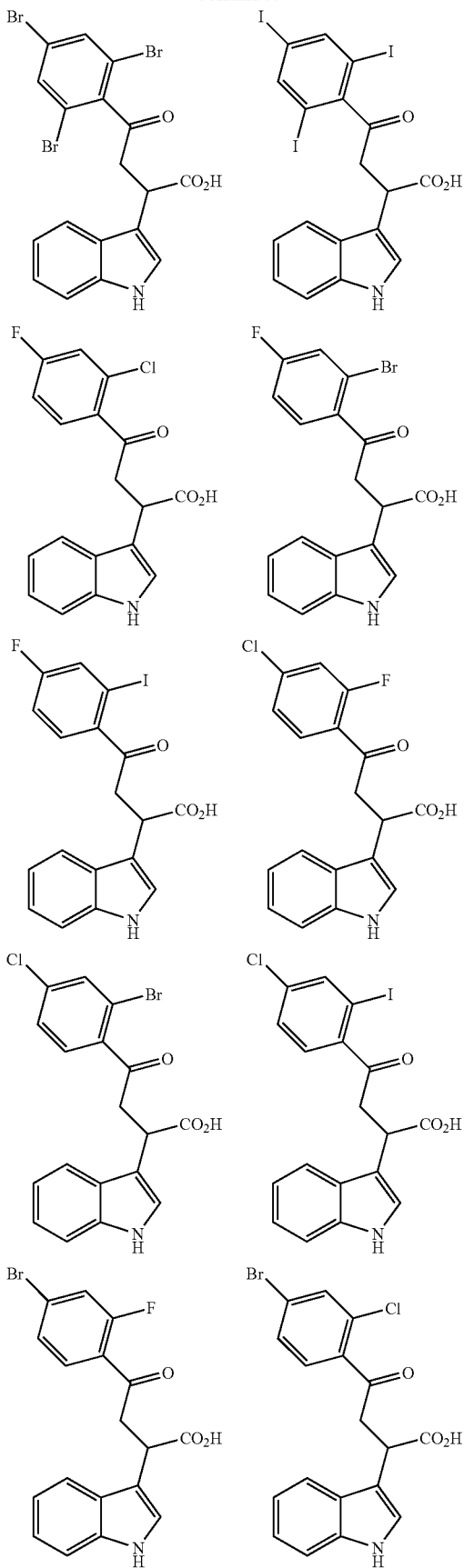
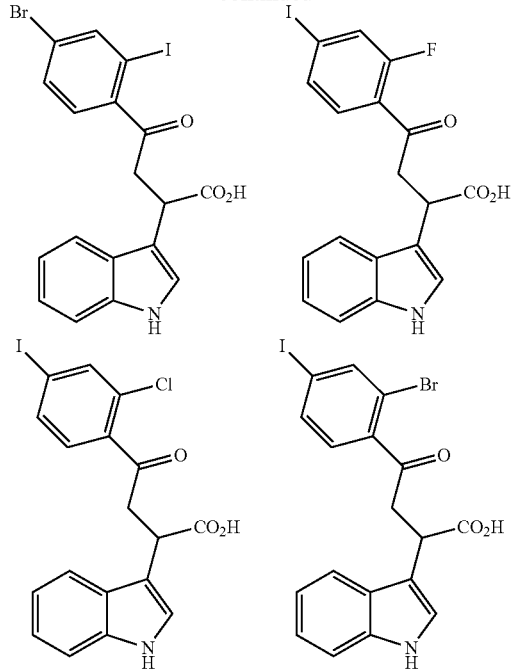
Of the above compounds, the compound of the formula (1-1) (4-(2,4-difluorophenyl)-2-(1H-indole-3-yl)-4-oxo-butanoic acid) is preferable.
Specific examples of the compound of formula (2) include the compounds shown below.
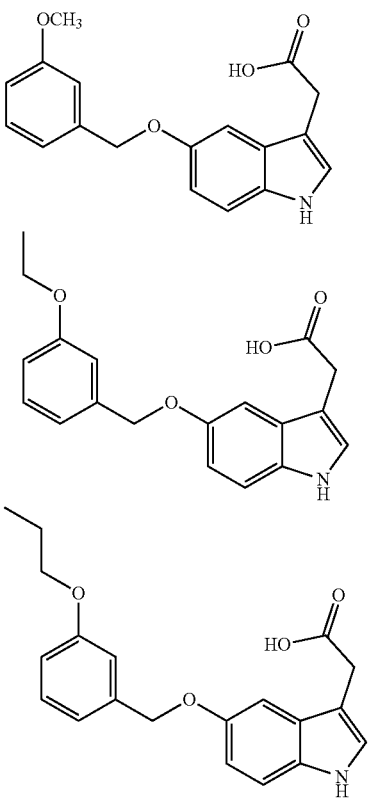

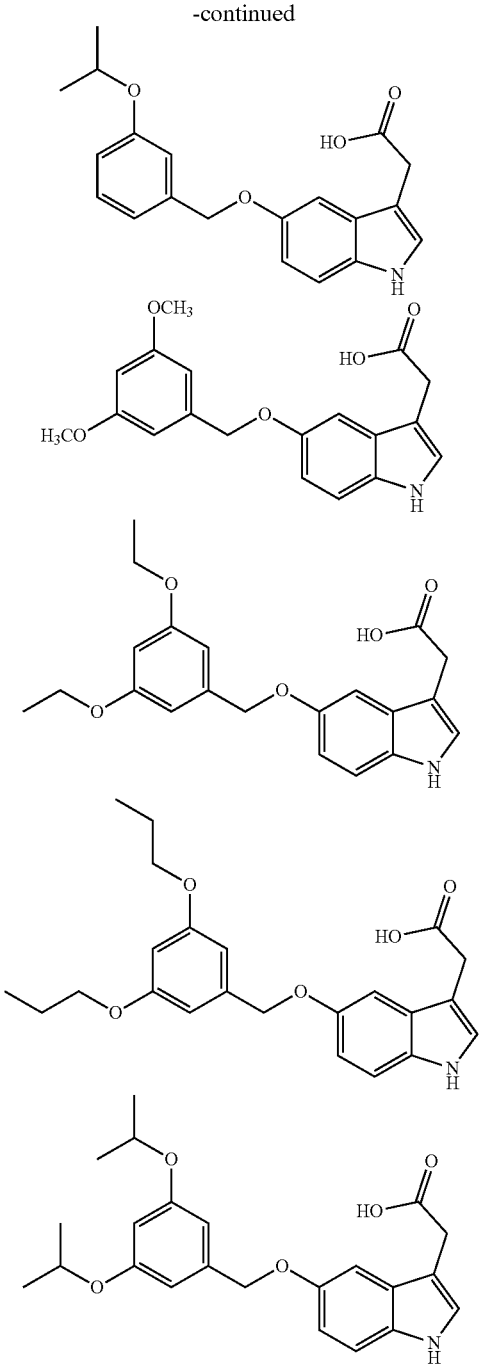

Of the above compounds, the compound of the formula (2-1) (5-(3,5-dimethoxybenzyloxy)-3-indoleacetic acid) is preferable.

When a compound selected from the present group of compounds has an asymmetric carbon atom and an asymmetric point related to axial asymmetry, such compound includes all possible optical isomers, and these optical isomers can be used in any ratio. For example, for a certain optically active compound, the enantiomers, racemates, or a mixture of the enantiomers in any ratio can be used, and when a plurality of asymmetric points is present, a mixture of diastereomers in any ratio may be used.

The physiologically acceptable salts in the present group of compounds include a metal salt produced from a base containing a metal such as aluminum, calcium, lithium, magnesium, potassium, sodium and zinc (for example, a hydroxide of these metals) and an organic salt produced from an organic base such as N,N'-dibenzylethylenediamine, chloroprocaine, choline, diethanolamine, ethylenediamine, N-methylglucamine, lysine and procaine.

Examples of the cancer for which the present prophylactic/therapeutic agent is administered include colorectal cancer (colon cancer or rectal cancer); stomach cancer; liver cancer; brain tumor; lung cancer (adenocarcinoma, squamous cell carcinoma, adenosquamous cancer, anaplastic cancer, large cell cancer, or small cell cancer); esophageal cancer; duodenal cancer; small intestinal cancer; skin cancer; breast cancer; prostate cancer; bladder cancer; vaginal cancer; cervical cancer; endometrial cancer; kidney cancer; pancreatic cancer; spleen cancer; tracheal cancer; bronchial cancer; head and neck cancer; gallbladder cancer; biliary cancer; testis cancer; ovarian cancer; cancer in bone tissue, cartilage tissue, adipose tissue, muscle tissue, nerve tissue, vascular tissue, or hematopoietic tissue (specifically, a sarcoma such as chondrosarcoma, Ewing's sarcoma, malignant hemangioendothelioma, malignant schwannoma, osteosarcoma, or soft tissue sarcoma; a granuloma such as hepatoblastoma, medulloblastoma, nephroblastoma, neuroblastoma, pancreatoblastoma, pleuropulmonary blastoma, or retinoblastoma; germ cell tumor; lymphoma; and leukemia), and of these, colorectal cancer can be suitably exemplified.

The present prophylactic/therapeutic agent may further contain an additive such as a conventional and pharmaceutically acceptable carrier, binder, stabilizer, excipient, diluent, pH buffer, disintegrant, isotonic agent, additive, coating agent, solubilizer, lubricant, solubilizing agent, lubricant, flavoring agent, sweetener, solvent, gelling agent, and nutritional agent, as necessary. Specific examples of such additive include water, physiological saline, an animal fat or oil, a vegetable oil, lactose, starch, gelatin, crystalline cellulose, gum, talc, magnesium stearate, hydroxypropyl cellulose, polyalkylene glycol, polyvinyl alcohol and glycerin.

Examples of the form of administration of the present prophylactic/therapeutic agent include oral administration, which administers in a dosage form such as a powder, granules, a tablet, a capsule, a syrup, or a suspension, and parenteral administration, which injects (for example, subcutaneous injection, intravenous injection, and intramuscular injection) a dosage form such as a solution, an emulsion, or a suspension, or administers intranasally in the form of a spray, and oral administration is preferable.

The dose of the present group of compounds in the present prophylactic/therapeutic agent is appropriately determined according to age, body weight, sex, symptoms, sensitivity to the drug, and the like, and is, for example, a dose in the range of 0.1 (μg/kg body weight/day) to 200 (mg/kg body weight/day). In the present Examples described later, the dose of 1 to 10 (mg/kg body weight/day) of the compound of the formula (1-1) (4-(2,4-difluorophenyl)-2-(1H-indole-3-yl)-4-oxo-butanoic acid) (hereinafter, may be referred to as "Present Compound #1" for convenience) and the dose of 1 to 10 (mg/kg body weight/day) of the compound of the formula (2-1) (5-(3,5-dimethoxybenzyloxy)-3-indoleacetic acid) (hereinafter, may be referred to as "Present Compound #2" for convenience) will be specifically shown by an experiment using model mice. Such dose is 81 to 810 (μg/kg body weight/day) when converted to the dose for humans, based on a human equivalent dose (HED) in mice of 12.3 (see the document "Guidance for Industry Estimating the Maximum Safe Starting Dose in Initial Clinical Trials for Therapeutics in Adult Healthy Volunteers"). Therefore, the dose of the present group of compounds in the present prophylactic/therapeutic agent is preferably 1.0 (μg/kg body weight/day) to 100 (mg/kg body weight/day), more preferably 10 (μg/kg body weight/day) to 50 (mg/kg body weight/day), still more preferably 20 (μg/kg body weight/day) to 10 (mg/kg body weight/day), still even more preferably 40 (μg/kg body weight/day) to 5.0 (mg/kg body weight/day), and most preferably 60 (μg/kg body weight/day) to 1.0 (mg/kg body weight/day). Note that the present prophylactic/therapeutic agent may be administered in a single or plurality of doses (for example, 2 to 4 doses) per day.

The present prophylactic/therapeutic agent may contain a component having a prophylactic or therapeutic action on cancer in addition to the present group of compounds, but it may also not contain any component (for example, a protein, DNA, RNA, a plant-derived extract, or a polymer) having a prophylactic or therapeutic action on cancer other than the present group of compounds since the present group of compounds alone also exerts the prophylactic or therapeutic action on cancer.

The method for synthesizing the compound selected from the present group of compounds can be exemplified below. However, the method is not limited to these methods, and a generally known synthetic method can be used.

Synthesis of Compound of Formula (1)

The compound of formula (1) can be obtained by performing a Michael reaction between the carboxylic acid compound of formula (3) and the indole derivative of formula (4) as shown below.

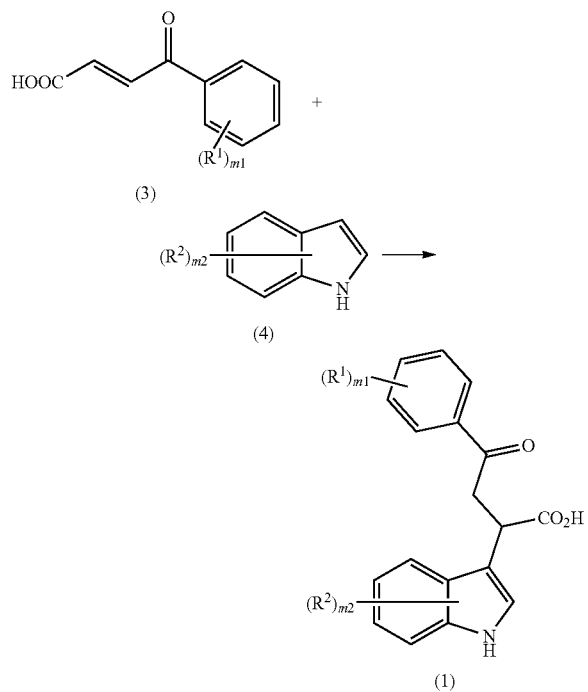

$R^1$, $R^2$, m1 and m2 in the above formulas (3) and (4) have the same definitions as $R^1$, $R^2$, m1 and m2 in the formula (1).

The carboxylic acid compound of the above formula (3) can be synthesized by a Friedel-Crafts reaction between the benzene derivative (5) and maleic anhydride as shown below. Such Friedel-Crafts reaction is performed by allowing a Lewis acid, phosphoric acid, polyphosphoric acid or the like to act as a catalyst, and aluminum chloride is suitably used as the catalyst.

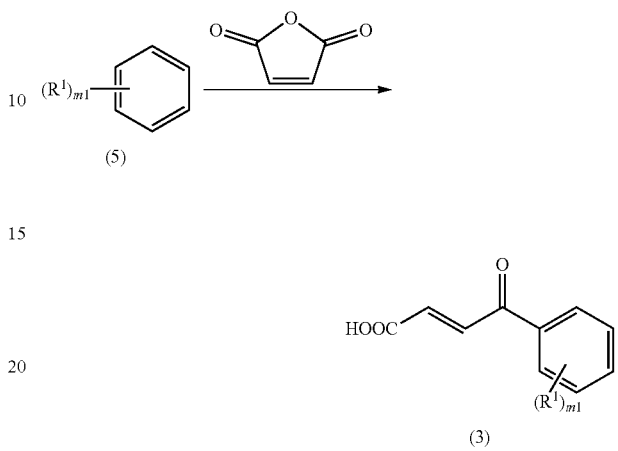

$R^1$ and m1 in the above formulas (5) and (3) have the same definitions as $R^1$ and m1 in the formula (1).

As the indole derivative of the above formula (4), a commercial product can be used. Examples of commercially available indole derivatives include 4-fluoroindole, 4-chloroindole, 4-bromoindole, 6-fluoroindole, 6-chloroindole, 6-bromoindole, and 5-methylindole.

In addition, the indole derivative of the above formula (4) can also be obtained by an organic synthesis technique using a publicly known organic chemical reaction. For example, when $R^2$ is a halogen atom, an indole derivative of the above formula (4) can be obtained by allowing a halogenating agent such as N-bromosuccinimide, N-chlorosuccinimide, or N-iodosuccinimide to act on a commercially available indole. Moreover, when $R^2$ is a C1-C6 alkyl group, a C2-C6 alkenyl group, a C2-C6 alkynyl group, or an organic oxy group represented by $OR^X$, an indole derivative of the above formula (4) can be obtained by halogenating a commercially available indole as described above, then performing a reaction with an organic lithium reagent such as alkyl-lithium, a Suzuki-Miyaura coupling reaction, or the like.

Synthesis of Compound of Formula (2)

The compound of formula (2) can be synthesized using a 5-hydroxy-3-indoleacetic acid derivative of formula (6) as a starting material. Specifically, the 5-hydroxy-3-indoleacetic acid of formula (6) is reacted in an alcohol such as methanol, ethanol, propanol or isopropanol under acidic conditions to be derived into an ester of formula (7).

Next, the compound of formula (9) can be synthesized by reacting the above ester with a halogen compound of formula (8) in the presence of a base. Examples of the above base include sodium hydride and a carbonate of an alkali metal such as lithium carbonate, sodium carbonate, potassium carbonate and cesium carbonate.

Subsequently, the compound of formula (2) is synthesized by hydrolyzing the ester moiety of the compound of formula (9).

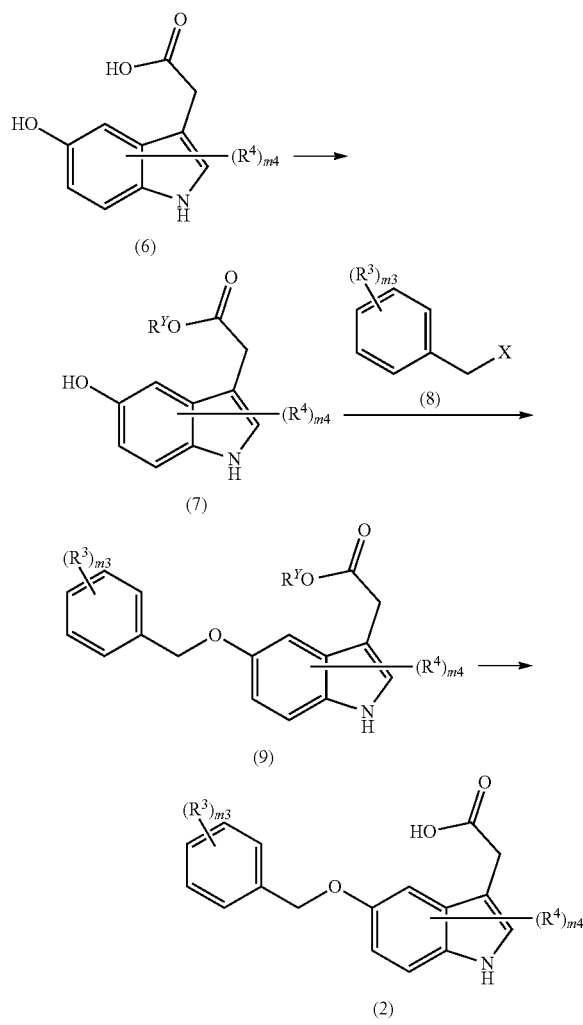

In the above formulas (7) and (9), $R^Y$ is a C1-C3 alkyl group such as a methyl group, an ethyl group, an n-propyl group and an isopropyl group.

In the above formula (8), X is a halogen atom such as a fluorine atom, a chlorine atom, a bromine atom and an iodine atom.

$R^3$, $R^4$, m3 and m4 in the above formulas (6), (7), (8) and (9) have the same definitions as $R^3$, $R^4$, m3 and m4 in the formula (2).

As the 5-hydroxy-3-indoleacetic acid derivative of above formula (6), a commercially available 5-hydroxy-3-indoleacetic acid or the like may be used, but the 5-hydroxy-3-indoleacetic acid derivative of the above formula (6) can also be obtained by an organic synthesis technique using a publicly known organic chemical reaction. For example, when $R^4$ is a halogen atom, the 5-hydroxy-3-indoleacetic acid derivative of the above formula (6) can be obtained by allowing a halogenating agent such as N-bromosuccinimide, N-chlorosuccinimide, or N-iodosuccinimide to act on a commercially available 5-hydroxy-3-indoleacetic acid. Moreover, when $R^4$ is a C1-C6 alkyl group, a C2-C6 alkenyl group, a C2-C6 alkynyl group, or an organic oxy group represented by $OR^X$, the 5-hydroxy-3-indoleacetic acid derivative of the above formula (6) can be obtained by halogenating a commercially available 5-hydroxy-3-indoleacetic acid as described above, then performing a reaction with an organic lithium reagent such as alkyllithium, a Suzuki-Miyaura coupling reaction, or the like.

As the halogen compound of the above formula (8), a commercially available benzyl bromide, 4-methylbenzyl bromide, 2-methylbenzyl bromide, 3-methylbenzyl bromide, 3-chlorobenzyl bromide, 2-chlorobenzyl bromide, 2,6-dichlorobenzyl bromide, 3-fluorobenzyl bromide, 4-fluorobenzyl bromide, 3,5-dimethoxybenzyl bromide or the like may be used, but the halogen compound of the above formula (8) can also be obtained by an organic synthesis technique using a publicly known organic chemical reaction. For example, when $R^3$ is a halogen atom, a halogen compound of the above formula (8) can be obtained by allowing a halogenating agent such as N-bromosuccinimide, N-chlorosuccinimide, or N-iodosuccinimide to act on a commercially available benzyl bromide. Moreover, when $R^3$ is a C1-C6 alkyl group, a C2-C6 alkenyl group, a C2-C6 alkynyl group, or an organic oxy group represented by $OR^X$, the above commercially available halogen compounds can be used, or the halogen compound of the above formula (8) can be obtained by halogenating a commercially available benzyl bromide as described above, then performing a reaction with an organic lithium reagent such as alkyllithium, a Suzuki-Miyaura coupling reaction, or the like.

All of the above organic reactions can each be performed in a solvent, but the solvent is appropriately selected according to the reaction temperature, the reaction product or the like. Moreover, the reaction temperature of the above organic reactions is appropriately selected according to conditions such as the boiling point of the solvent used. When a solvent is used in the above organic reactions, the obtained reaction solution may be concentrated as needed and then the residue may be used as it is in the next reaction, or it may be used as the compound of the formula (1) after an appropriate post-treatment. Specific examples of the method for post-treatment include an extraction treatment and/or a publicly known purification such as crystallization, recrystallization, and chromatography.

Hereinafter, the present invention will be described more specifically by Examples, but the technical scope of the present invention is not limited to these Examples.

EXAMPLES

1. Materials and Methods
[Present Group of Compounds]

The two specific compounds (Present Compound #1 and Present Compound #2) included in the present group of compounds were synthesized according to the methods for synthesizing the Compound #5 (corresponding to the Present Compound #1) and the Compound #35 (corresponding to the Present Compound #2) described in patent document 4 (International Publication No. WO 2014/080640 pamphlet), respectively. In the cell migration test, Present Compound #1 and Present Compound #2 were used after being dissolved in 100% DMSO.

[Cell Culture]

Cells of the human colorectal cancer cell line HCT116 (obtained from ATCC) were cultured and maintained in a DMEM (Dulbecco's Modified Eagle Medium) culture solution (manufactured by Sigma-Aldrich) containing 10% fetal bovine serum (FBS) (manufactured by Biowest) and 1% penicillin-streptomycin (manufactured by Thermo Fisher Science) under the conditions of 5% $CO_2$/20% $O_2$ and 37° C.

[Preparation of Each Group]

Model mice of colorectal cancer were prepared using azoxymethane (AOM; manufactured by Wako Pure Chemical Industries, Ltd.) and dextran sulfate sodium (DSS, manufactured by MP Biomedicals). Specifically, 5-week-old male ICR mice (produced by CLEA Japan) were first acclimated and bred for 1 week. At 6 weeks of age, the mice were randomly divided in a control group and 5 colorectal cancer groups (placebo group, Present Compound #1[1] group, Present Compound #1[10] group, Present Compound #2[1] group, and Present Compound #2[10] group), and 10 (mg/kg body weight) of AOM was intraperitoneally administered to the colorectal cancer groups. Seven days later, the mice were allowed to freely drink 2.5% (w/v) DSS for 1 week, and then tap water for 14 days. This administration of DSS was performed for cycles (70 days in total) to prepare model mice of colorectal cancer. When the above AOM was intraperitoneally administered (that is, at 6 weeks of age), physiological saline solutions containing 1 (mg/kg body weight/day) and 10 (mg/kg body weight/day) of the Present Compound #1 were orally administered for 70 consecutive days thereafter to the Present Compound #1(1) group and the Present Compound #1(10) group, respectively, physiological saline solutions containing 1 (mg/kg body weight/day) and 10 (mg/kg body weight/day) of the Present Compound #2 were orally administered for 70 consecutive days thereafter to the Present Compound #2(1) group and the Present Compound #2(10) group, respectively, and a physiological saline solution was orally administered for 70 consecutive days thereafter to the placebo group. In addition, to the control group, a physiological saline solution was orally administered at 6 weeks of age for 70 consecutive days thereafter. All mice were sacrificed and the colons were harvested immediately after the end of the third cycle. The colons were photographed in full length and the colon length (see FIG. 1B), as well as the tumor area in the colon (see FIG. 1A), the ratio of tumor area in the colon (see FIG. 2A), and the number of tumors having a diameter of more than 2 mm (see FIG. 2B) were measured. Note that, for the tumors, the elevated lesions that were thought to contain cancer were visually observed in the colon (large intestine), and the area of these elevated lesions (that is, the tumors) and the total colon area were calculated by NIH Image J version 1.51 (US National Institutes of Health, MD, http://imagej.nih.gov/ij/index.html). The ratio of tumor area in the colon was calculated based on the formula "(elevated lesion area/total colon area)×100".

[Cell Migration Test]

$7.5 \times 10^4$ cells of the colorectal cancer cell line HCT116 were seeded in each well of the Corning Fluoroblok 24-Multiwell Insert Systems (pore size: 8.0 μm) (manufactured by Corning), and cultured for 48 hours in FBS-free DMEM culture solution or FBS-free DMEM culture solution containing 50 μM of the Present Compound #2. Note that a DMEM culture solution containing 20% FBS, which is an attractant, was added to the chamber at the bottom of the plate. The migrating cells that had passed through the membrane on the lower surface of the cell culture insert were stained using a Diff-Quik kit (manufactured by Sysmex), the membrane was air-dried, and then the number of cells was measured in three fields of view using a phase-contrast microscope.

[Statistical Analysis]

Student's t-test was used for the comparison between two groups, and Dunnet's test or Tukey's test was used for the comparison between three groups. The survival rate (see FIG. 3) was evaluated by a log-rank test using the Kaplan-Meier survival curve. JMP version 14 (manufactured by SAS Institute) was used for statistical analysis. For all test results, p-values less than 0.05 were considered statistically significant.

2. Results

The tumor area in the colon was smaller in the colorectal cancer groups administered with the present group of compounds (that is, the Present Compound #1(10) group, the Present Compound #2(1) group, and the Present Compound #2(10) group) than in the colorectal cancer group not administered with the present group of compounds (that is, the placebo group) (see FIG. 1A). In addition, the colon length was shortened in the colorectal cancer group not administered with the present group of compounds (that is, the placebo group) compared to the control group, whereas such shortening was suppressed in the colorectal cancer groups administered with the present group of compounds (that is, the Present Compound #1(10) group, the Present Compound #2(1) group, and the Present Compound #2(10) group) (see FIG. 1B).

Moreover, the ratio of tumor area in the colon was smaller in the colorectal cancer groups administered with the present group of compounds (that is, the Present Compound #1(1) group, the Present Compound #1(10) group, and the Present Compound #2(10) group) than in the colorectal cancer group not administered with the present group of compounds (that is, the placebo group) (see FIG. 2A). Further, the number of tumors having a diameter of more than 2 mm was smaller in the colorectal cancer groups administered with the present group of compounds (that is, the Present Compound #1(1) group, the Present Compound #1(10) group, and the Present Compound #2(10) group) than in the colorectal cancer group not administered with the present group of compounds (that is, the placebo group) (see FIG. 2B).

Furthermore, 4 out of 8 mice died in the placebo group, whereas all 8 mice survived in the Present Compound #2(10) group (see FIG. 3).

These results indicate that the present group of compounds has a suppressive effect on the growth of cancer cells associated with the onset of cancer and an improving effect of the decrease in survival rate due to cancer.

In addition, the cell migration level of the colorectal cancer cells was lower when the colorectal cancer cells were cultured in the presence of the Present Compound #2 than when the colorectal cancer cells were cultured in the absence of the Present Compound #2 (See FIG. 4). These results indicate that the present group of compounds reduces the migration level of cancer cells and has a suppressive effect on cancer metastasis.

INDUSTRIAL APPLICABILITY

The present invention contributes to the prevention or treatment of cancer.

PRIOR ART DOCUMENTS

Patent Documents

Patent Document 1: International Publication No. WO 2014/080640 pamphlet

Patent Document 2: International Publication No. WO 2017/073060 pamphlet

The invention claimed is:

1. A method for treating cancer, comprising administering one or more compounds selected from the compound of the following formula (1-1), the compound of the following formula (2-1):

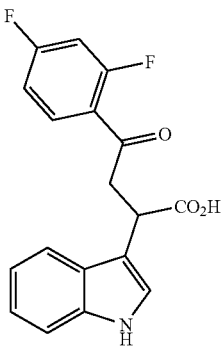
(1-1)

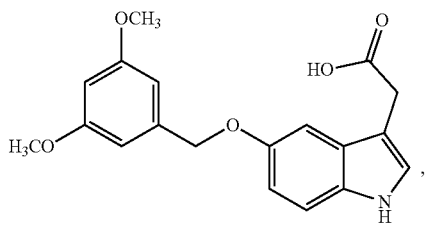
(2-1)

or a pharmacologically acceptable salt thereof, to a subject in need of treatment of cancer.

2. The method according to claim 1, wherein the cancer is a colorectal cancer.

3. The method according to claim 1, wherein the one or more compounds are orally administered.

4. The method according to claim 2, wherein the one or more compounds are orally administered.

* * * * *